(12) United States Patent
Ortiz et al.

(10) Patent No.: US 7,997,898 B2
(45) Date of Patent: Aug. 16, 2011

(54) ILLUMINATED ORTHODONTIC RETAINER

(76) Inventors: Wanda Ortiz, Westbury, NY (US); Myrna Ortiz, Westbury, NY (US)

(*) Notice: Subject to any disclaimer, the term of this patent is extended or adjusted under 35 U.S.C. 154(b) by 623 days.

(21) Appl. No.: 12/007,506

(22) Filed: Jan. 11, 2008

(65) Prior Publication Data
US 2009/0181338 A1 Jul. 16, 2009

(51) Int. Cl.
*A61C 3/00* (2006.01)

(52) U.S. Cl. .............................. 433/6; 433/29

(58) Field of Classification Search ............ 433/6, 18, 433/29; 362/103, 104, 804
See application file for complete search history.

(56) References Cited

U.S. PATENT DOCUMENTS

| 5,989,023 A * | 11/1999 | Summer et al. ............. 433/69 |
| 2004/0043349 A1* | 3/2004 | Liao ........................ 433/29 |
| 2004/0264173 A1* | 12/2004 | Vanderschuit ........... 362/103 |
| 2007/0147025 A1* | 6/2007 | Shirey .................... 362/103 |

* cited by examiner

*Primary Examiner* — Chris L Rodriguez
*Assistant Examiner* — Eric Rosen
(74) *Attorney, Agent, or Firm* — H. Jay Spiegel

(57) ABSTRACT

A standard orthodontic retainer is modified on its surface opposite the palate and facing the patient's tongue with a light, a small battery to provide power for the light means, and a frame beneath the light that allows a template to be removably slid into the frame. The template consists of a design such as a heart, a letter of the alphabet, a symbol, or other design that, when the light is activated, shines the pattern onto the top of the tongue of the user. The template can be made so that the design displayed on the user's tongue is of any desired color or color combination. Alternatively, the color of the displayed design may be created by the color of the light or by an additional template consisting of an optical filter providing the desired color.

18 Claims, 2 Drawing Sheets

ILLUMINATED ORTHODONTIC RETAINER

BACKGROUND OF THE INVENTION

The present invention relates to an illuminated orthodontic retainer. The inventive retainer is intended to illuminate a portion of the tongue of the user for aesthetic purposes. In the prior art, orthodontic retainers are well known and are used for the purpose of facilitating straightening of the user's teeth and aligning their bite. For this purpose, such retainers have a palatal vault portion typically custom made of a soft plastic material that underlies the palate of the user and has wiring surrounding the palatal vault and specifically designed to engage specified teeth so that when the retainer is worn, the specified teeth are straightened so that the user's bite is corrected.

Heretofore, orthodontic retainers have been limited in their construction to merely facilitating correction of the user's bite. With the advent of tattoos and the use of illumination means on clothing including hats and shirts, there has evolved a desire on the part of the consuming public to use the human body as a "canvas" on which artistic designs are displayed. Within the mouth, grilles are sometimes designed to fit over the teeth for aesthetic reasons. Additionally, sometimes teeth are capped with aesthetic designs including the use of precious stones and other features. Many of these aesthetic products such as tooth caps, tattoos, and others are either irreversible or expensive and/or difficult to reverse. As such, if an invention could be devised permitting marking of the body for aesthetic reasons, but in which the marking is not permanent, such an invention would be attractive to the consuming public. It is with this thought in mind that the present invention was developed.

The following prior art is known to Applicants:

U.S. Pat. No. 6,089,864 to Buckner et al. discloses a biofeedback data acquisition tooth guard and the method of its manufacture and use. This device is designed to evaluate, detect and treat people who suffer from the chronic grinding of teeth known as "bruxing." The apparatus includes a pressure sensor contained therein and electronics for detecting activation of a sensor due to bruxing.

U.S. Pat. No. 6,499,995 to Schwartz discloses a phosphorescent dental appliance that is made of a material permitting it to glow in the dark. The Schwartz device is activated through shining of light thereon and is made of a phosphorescent material. The device of Schwartz does not contemplate the illumination means and pattern that are disclosed in the present invention.

U.S. Pat. No. 6,702,575 to Hilliard discloses a method and apparatus for orthodontic treatment that includes a removable orthodontic aligner. The Hilliard device contemplates the addition of auxiliary devices removably attachable thereto which include ornamental or decorative designs. Hilliard fails to teach or suggest the illumination means contemplated in the present invention.

U.S. Pat. No. 6,837,606 to Baillie-Hamilton discloses light emitting device and arrays thereof. Baillie-Hamilton fails to contemplate the use of illumination means in the environment contemplated in the present invention.

SUMMARY OF THE INVENTION

The present invention relates to an illuminated orthodontic retainer. The present invention includes the following interrelated objects, aspects and features:

(1) In a first aspect, the present invention contemplates modifications to an orthodontic retainer as commonly used by orthodontists in facilitating the straightening of a person's teeth and alignment of their bite.

(2) In such an orthodontic retainer, the structures include a maxillary palatal vault made of a material such as soft plastic and molded to closely match the contours of the palate of the patient. About the periphery of the maxillary palatal vault, a plurality of wires are provided in specific locations so that when the retainer is worn, those wires interact with the patient's teeth to cause the teeth to be straightened and the bite to be aligned.

(3) The present invention consists of a modification of the structure of a standard orthodontic retainer. In particular, the present invention is mounted on the undersurface of the maxillary palatal vault, the surface opposite the palate and facing the patient's tongue.

(4) The invention consists of a source of light or illumination means, a source of power comprising a small battery to provide power for the illumination means, and a frame beneath the illumination means that allows pattern means comprising a template to be slid into the frame or removed therefrom.

(5) The template consists of a design such as a heart, a letter of the alphabet, a symbol, or other design that, when the illumination means is activated, shines the pattern onto the top of the tongue of the user.

(6) The template can be made in such a manner that the design displayed on the user's tongue is of any desired color or color combination. Alternatively, the color of the displayed design may be created by the color of the illumination means or by an additional template consisting of an optical translucent filter providing the desired color.

(7) An on-off switch is provided at a suitable location to facilitate activating and deactivating the device.

(8) If desired, the maxillary palatal vault may be made of a thickness allowing the illumination means, the battery and the wiring to be imbedded therewithin, with the light exposed downwardly, and with the frame adjacent the lower surface of the maxillary palatal vault.

As such, it is a first object of the present invention to provide an illuminated orthodontic retainer.

It is a further object of the present invention to provide such a device in which illumination means is imbedded in the maxillary palatal vault of the retainer.

It is a still further object of the present invention to provide such a device in which a battery is also imbedded in the maxillary palatal vault with wiring connecting the battery and illumination means.

It is a still further object of the present invention to provide such a device in which a template is slidably received on the vault.

It is a still further object of the present invention to provide such a device in which the template may easily be removed and replaced with a template bearing another design.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1:
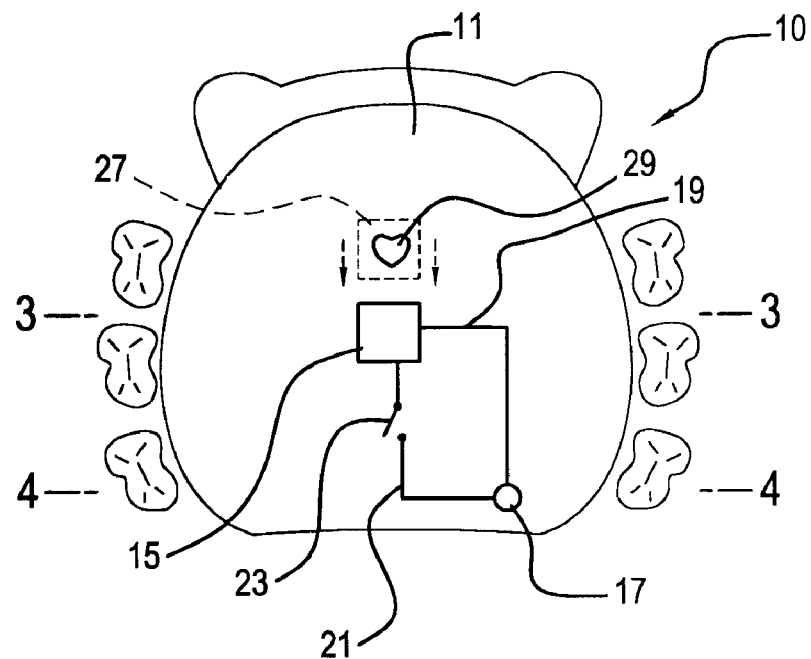
FIG. 1 shows a bottom view of the inventive illuminated orthodontic retainer.
Figure 2:
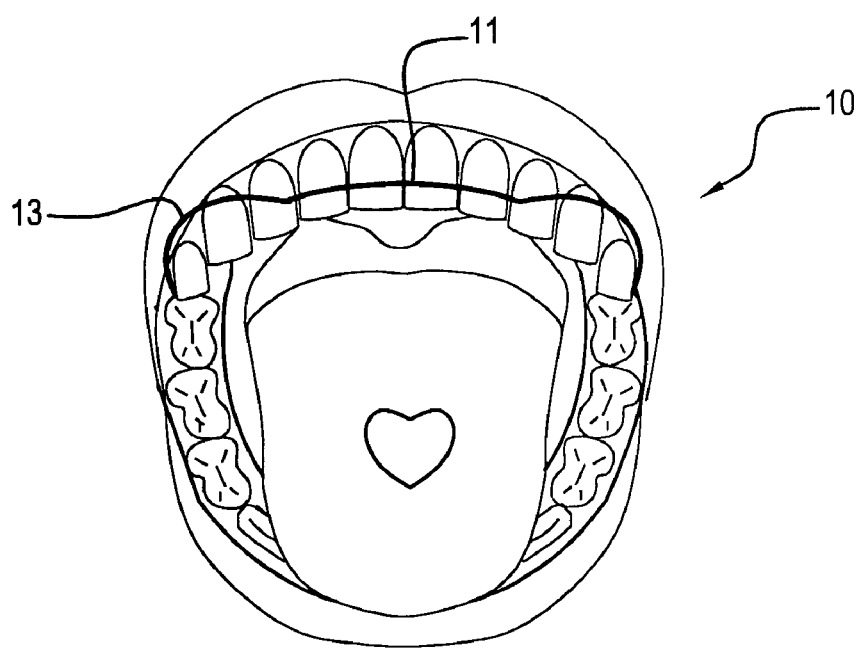
FIG. 2 shows a front view of the inventive retainer.
Figure 3:
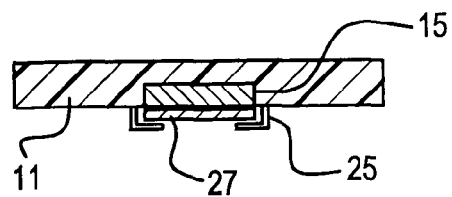
FIG. 3 shows a cross-sectional view along the line 3-3 of FIG. 1.

With reference to FIGS. 1-6, the present invention is generally designated by the reference numeral 10 and is seen to include a maxillary palatal vault 11 having peripheral wires 13 (FIG. 2) arranged in a manner well known to those of ordinary skill in the art to facilitate straightening of teeth and alignment of the bite. As best seen in FIGS. 1 and 3, the vault 11 has embedded therein illumination means 15 consisting of a light such as a thin light emitting diode (LED) or a plurality of pixels that may be formed by a single lightbulb and a pixelated lens such as commonly seen on a vehicle tail light.

Figure 4:
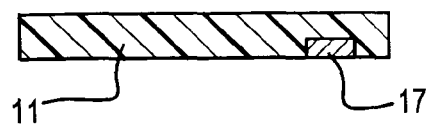
FIG. 4 shows a cross-sectional view along the line 4-4 of FIG. 1.

With reference to FIGS. 1 and 4, a battery 17 is also embedded in the vault and electrical wires 19 and 21 complete a circuit between the illumination means 15 and the battery 17. Additionally, a switch 23 is schematically shown in FIG. 1 and may be of any desired design such as a pushbutton switch, a toggle switch, or any other switch that may be miniaturized so that it can be mounted on the vault 11 without irritation to the mouth of the user.

Figure 5:
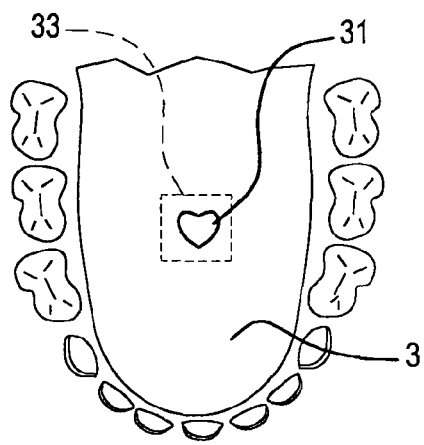
FIG. 5 shows a top view of the tongue with an illuminated design visible thereon.
Figure 6:
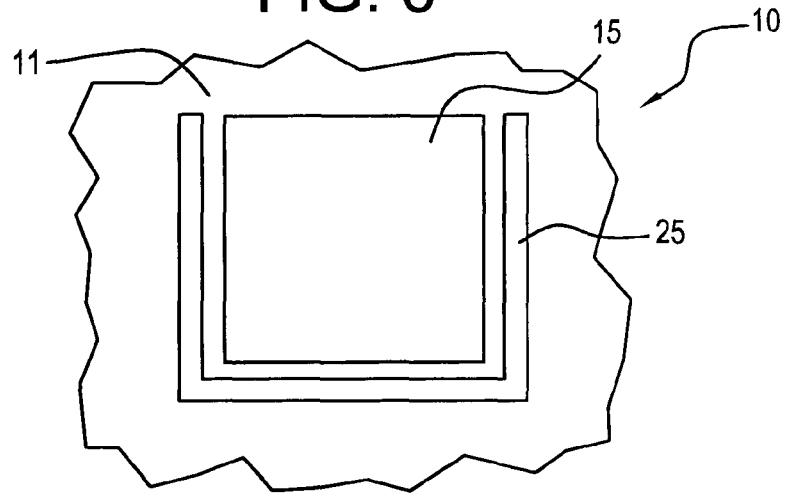
FIG. 6 shows an enlarged bottom view of the vault showing the frame used to removably retain a template under the illumination means.

As seen in FIGS. 3 and 6, a frame 25 is located on the vault 11 surrounding three sides of the illumination means 15. As best seen in FIG. 3, the frame 25 comprises an inverted L-shaped cross-section that provides a recess allowing removable receipt of a template 27 (FIGS. 1 and 3). The template may be of any desired material and preferably includes a specially shaped opening such as the heart-shaped opening 29 seen in FIG. 1. Such an opening results in a heart-shaped lighted area 31 displayed on the tongue 3 of the user. FIG. 5 also shows a dotted line 33 that shows the outline of the template 27. The template 27 may be made of any desired material including opaque materials and translucent materials. When the template 27 is made of an opaque material, the light may only shine through an opening within the shape, for example 29 (FIG. 1). In that embodiment, the color of the design 31 displayed on the tongue 3 will correspond to the color of the light emanating from the illumination means 15. That color may easily be determined by providing a light of a desired color or a white light with a translucent filter mounted thereover.

In similar fashion, the template 27 may be made of a translucent material in any desired color. For example, the template could be made of a material that is opaque except for a translucent portion in a desired shape and made in a desired color.

The design that creates the design 31 on the tongue 3 as seen in FIG. 5 may be any desired design, shape and/or color to result in a desired display on the user's tongue.

The battery 17 may be any desired type of battery with smaller and lighter batteries being more desirable. Batteries used for hearing aids and watches are suitable for use in association with the present invention.

If desired, the vault 11 may be made of a material that carries a desirable flavor such as cherry, blueberry, orange, etc. The frame may be made of any suitable plastic or metal so long as it does not have any sharp edges that could cut the tongue or mouth of the user. As explained above, the illumination means 15 may comprise any miniature light suitable for embedding in the vault 11. Examples of such lights include light emitting diodes (LED) and lights covered by pixelated filters to cause light diffusion and uniformity of display.

As such, an invention has been disclosed in terms of preferred embodiments thereof which fulfill each and every one of the objects of the invention as set forth hereinabove, and provide a new and useful illuminated orthodontic retainer of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

The invention claimed is:

1. In an orthodontic retainer including a maxillary palatal vault having an upper surface facing a user's palate and an undersurface facing a user's tongue, the improvement comprising illumination means comprising:
   a) a source of light mounted on said vault and oriented to shine light toward a user's tongue when said retainer is received within said user's mouth;
   b) a source of power connected to said source of light;
   c) pattern means including an opening for causing light emanating from said source of light to be displayed in a pattern corresponding to a shape of said opening, said pattern means comprising a template removably mounted beneath said source of light so that light shines through said opening when said source of light is activated;
   d) said pattern configured to shine on said tongue when said retainer is positioned in a user's mouth.

2. The retainer of claim 1, wherein said source of light is embedded in said undersurface of said vault.

3. The retainer of claim 2, wherein said source of light comprises at least one light emitting diode (LED).

4. The retainer of claim 3, wherein said at least one LED comprises a plurality of LEDs.

5. The retainer of claim 2, wherein said source of light includes a filter.

6. The retainer of claim 5, wherein said filter is translucent and made of a desired color.

7. The retainer of claim 5, wherein said filter is pixelated.

8. The retainer of claim 1, further including a frame mounted surrounding said source of light and sized to removably receive said template.

9. The retainer of claim 1, wherein said opening is of a desired shape, said pattern configured to shine on said tongue in substantially said desired shape when said retainer is positioned in a user's mouth.

10. The retainer of claim 9, wherein said desired shape comprises a heart.

11. The retainer of claim 9, wherein said template is generally rectangular.

12. The retainer of claim 1, further including an on-off switch connected between said source of power and source of light.

13. The retainer of claim 12, wherein said source of power comprises a battery.

14. The retainer of claim 13, wherein said battery is embedded within said vault.

15. The retainer of claim 1, further including electrically conducting wires connected between said source of light and source of power.

16. In an orthodontic retainer including a maxillary palatal vault having an upper surface facing a user's palate and an undersurface facing a user's tongue, the improvement comprising illumination means comprising:
  a) a source of light comprising at least one light emitting diode (LED) embedded in said vault and oriented to shine light toward a user's tongue when said retainer is received within said user's mouth;
  b) a source of power connected to said source of light and embedded in said vault, and an on-off switch connected between said source of power and source of light;
  c) pattern means including an opening for causing light emanating from said source of light to be displayed in a pattern corresponding to a shape of said opening, said pattern means comprising a template with said opening therethrough, said template being removably mounted beneath said source of light so that light shines through said opening when said source of light is activated, and a frame mounted surrounding said source of light and sized to removably receive said template, said opening being of a desired shape, said pattern configured to shine on said tongue in substantially said desired shape when said retainer is positioned in a user's mouth.

17. The retainer of claim 16, wherein said at least one LED comprises a plurality of LEDs.

18. The retainer of claim 16, wherein said source of light includes a filter, said filter being translucent and made of a desired color.

* * * * *